(12) United States Patent
Unluturk et al.

(10) Patent No.: US 7,526,529 B2
(45) Date of Patent: Apr. 28, 2009

(54) APPARATUS AND METHOD FOR PRESENTING DATA AND SENDING A MESSAGE

(75) Inventors: Mehmet Unluturk, Chicago, IL (US); Craig S. Bixler, Saint Charles, IL (US); Ping Li, Naperville, IL (US)

(73) Assignee: GE Security, Inc., Bradenton, FL (US)

( * ) Notice: Subject to any disclaimer, the term of this patent is extended or adjusted under 35 U.S.C. 154(b) by 584 days.

(21) Appl. No.: 11/142,342

(22) Filed: Jun. 2, 2005

(65) Prior Publication Data

US 2006/0112187 A1    May 25, 2006

Related U.S. Application Data

(60) Provisional application No. 60/575,818, filed on Jun. 2, 2004.

(51) Int. Cl.
*G06F 15/16* (2006.01)

(52) U.S. Cl. ............ 709/217; 340/286.07; 340/539.12; 600/300; 705/3

(58) Field of Classification Search ................. 709/201, 709/206, 207; 718/101; 706/924; 340/286.07, 340/539.12; 600/300; 705/3
See application file for complete search history.

(56) References Cited

U.S. PATENT DOCUMENTS

| | | | | |
|---|---|---|---|---|
| 5,576,952 | A * | 11/1996 | Stutman et al. | 600/300 |
| 6,067,524 | A * | 5/2000 | Byerly et al. | 705/3 |
| 7,143,139 | B2 * | 11/2006 | Burbeck et al. | 709/206 |
| 7,292,135 | B2 * | 11/2007 | Bixler et al. | 340/286.07 |
| 7,430,608 | B2 * | 9/2008 | Noonan et al. | 709/230 |
| 2004/0111478 | A1 * | 6/2004 | Gross et al. | 709/206 |
| 2005/0108341 | A1 * | 5/2005 | Mathew et al. | 709/206 |
| 2006/0053034 | A1 * | 3/2006 | Hlatheln et al. | 705/2 |
| 2006/0112187 | A1 * | 5/2006 | Unluturk et al. | 709/238 |
| 2006/0214786 | A1 * | 9/2006 | Bixler et al. | 340/539.12 |

* cited by examiner

*Primary Examiner*—Michael Won
(74) *Attorney, Agent, or Firm*—Global Patent Operation

(57) ABSTRACT

An apparatus and method for receiving relevant data, presenting the relevant data to users, and enabling users to construct and route an outgoing message. Using this apparatus and method, hospitals can provide efficient and personalized service by viewing up-to-date information about each admitted patient and, if necessary, routing relevant portions of the information, via a text message, to those responsible for patient care.

20 Claims, 3 Drawing Sheets

APPARATUS AND METHOD FOR PRESENTING DATA AND SENDING A MESSAGE

CROSS-REFERENCE TO RELATED APPLICATIONS

This application claims priority to U.S. patent application entitled, AUTOMATIC AND MANUAL HOSPITAL STAFF MESSAGING WITH PATIENT INFORMATION, filed Jun. 2, 2004, having a Ser. No. 60/575,818, the disclosure of which is hereby incorporated by reference in its entirety.

FIELD OF THE INVENTION

The present invention relates generally to the field of communication networks. More particularly, the present invention relates to an apparatus and method for receiving relevant data, presenting the relevant data to users, and enabling users to construct and route an outgoing message.

BACKGROUND OF THE INVENTION

Many hospitals use hand-written greaseboards to broadcast patient information to hospital staff and thereby facilitate efficient healthcare service. These greaseboards are large and prominently displayed such that patient information is readily available to hospital staff. A negative result of these large and prominently displayed greaseboards is non-hospital staff, for example visitors, also have access to patient information. Thus, traditional hand-written greaseboards create patient privacy concerns. Further, because of public accessibility, these traditional hand-written greaseboards may violate the Health Insurance Portability & Accountability Act of 1996, which was enacted, in part, to ensure patient privacy.

Instead of traditional hand-written greaseboards, some hospitals now use electronic greaseboards. Typically, electronic greaseboards are smaller than traditional greaseboards and therefore can be discretely located in areas where only those having privy to patient information have access. However, these electronic greaseboards are deficient because they do not provide for constructing and routing a message. For example, electronic greaseboards found in the prior art do not include the feature of constructing and routing a message comprising information obtained from the greaseboard directly to hospital staff members such that they may provide immediate and efficient services.

There exists a need for an electronic greaseboard that can alert hospital staff to patient needs and provide relevant information about the patient so the staff member can provide efficient service. The presently claimed invention enables an operator to search for and obtain information regarding a patient and instantaneously send a message to the responsible caregiver alerting them of patient needs.

Accordingly, it is desirable to provide an apparatus and method for receiving relevant data, presenting the relevant data to users, and enabling users to construct and route an outgoing message. Hospitals can provide efficient and personalized service by using this apparatus and method to access and view up-to-date information about each admitted patient and, if necessary, route relevant portions of the information, via a text message, to those responsible for caring for the patient.

SUMMARY OF THE INVENTION

The foregoing needs are met, to a great extent, by the present invention, wherein in one aspect an apparatus is provided that in some embodiments receives relevant data, presents the relevant data to users, and enabling users to construct and route an outgoing message.

In accordance with one embodiment of the present invention is an apparatus linked to a network and configured to display data and provide a message, wherein the apparatus comprises: a transaction table device in communication with a data source located in the network, wherein the transaction table device is configured to receive data; an electronic greaseboard device in communication with the transaction table device and configured to display data; and a message generator in communication with the electronic greaseboard device and configured to provide the message.

In accordance with another embodiment of the present invention is a method for communicating, comprising receiving data from a data source; storing data in a transaction table device; transmitting data to an electronic greaseboard device configured to present data; generating a message via a message generator; and routing the message to an output device.

In accordance with yet another embodiment of the present invention is an apparatus for communicating, comprising means for an apparatus linked to a network and configured to display data and provide a message, wherein the apparatus comprises a data source configured to provide a plurality of transactions; a transaction table device linked to the data source and configured to receive the transactions; a system status table device linked to the transaction table device and configured to organize the transactions; an electronic greaseboard device linked to the transaction table device and the system status table device and configured to display the transactions; and a message generator linked to the electronic greaseboard device and configured to provide the message.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention

DETAILED DESCRIPTION

Figure 1:
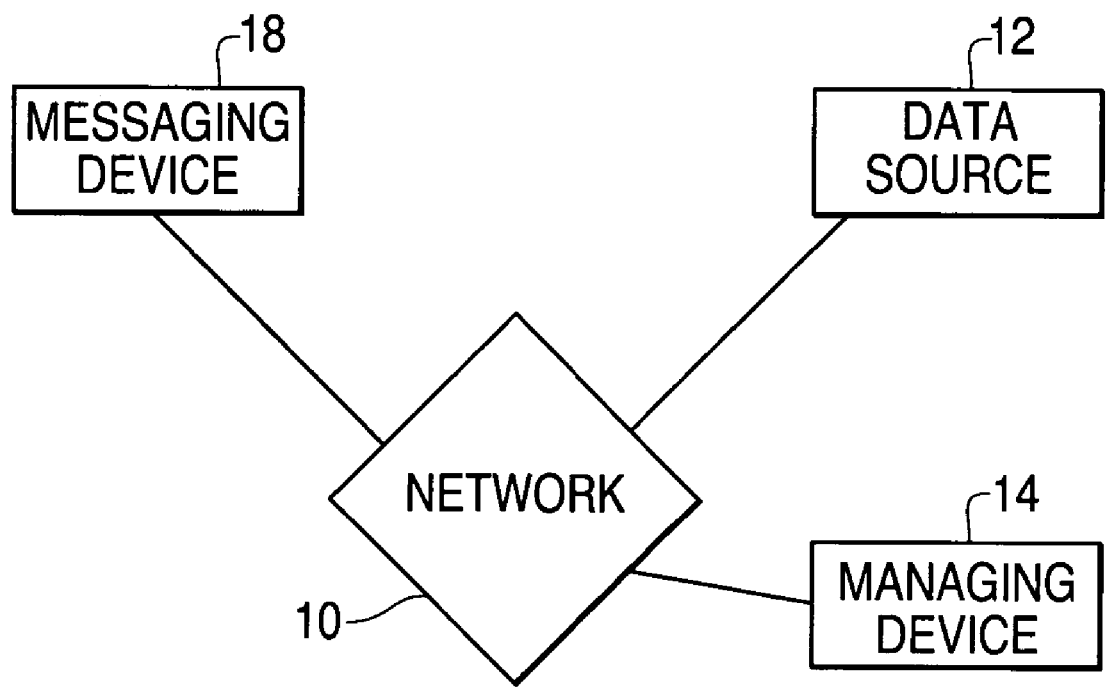
FIG. 1 is a block diagram illustrating a communication network according to the preferred embodiment of the present invention.

The invention will now be described with reference to the drawing figures, in which like reference numerals refer to like parts throughout. The present invention provides an apparatus and method for receiving relevant data, presenting the relevant data to users, and enabling users to construct and route an outgoing message. An embodiment in accordance with the present invention provides a data source, a managing device, a messaging device, and a network linking the aforementioned devices. The managing device is in communication with the data source. In operation, the data source updates the managing device when data is newly added or modified, and the managing device presents the relevant data to users. Based on the relevant data, the user can utilize the managing device to construct and route an outgoing message to the messaging device.

FIG. 1 is an exemplary communication network 10 according to the disclosed apparatus and method. As shown in FIG. 1, the exemplary network 10 includes a data source 12, a managing device 14, and a messaging device 18. It should be appreciated that the above mentioned components 12-18 can be linked together by any architecture that is well known to those of ordinary skill in the art.

The communication network 10, for example, facilitates communication among hospital staff and between hospital staff and patients. For example, a hospital staff member can access the managing device 14 where relevant data is presented. Based on the presented data, the staff member can construct an outgoing message and send the message to appropriate hospital staff via the messaging device 18. Upon receiving the message, the hospital staff can establish two-way communication with the relevant party, for example, the particular patient for which the message is concerned.

The data source 12 is, for example, a nurse call device, where the patient can provide data to the managing device 14 by actuating an indicator button, such as a bathroom button, an emergency button, a staff assistant button, or a nurse call button. Also, the data source 12 can be an automated machine, for example, a heart monitor that can automatically provide data to the managing device 14. The data source 12 is in communication with the managing device 14. For example, when the data source 12 is a nurse call device or an automated machine, the data source 12 provides updated data regarding its location, i.e., intensive care unit or pediatrics, and the status or condition of the patient.

The data source 12 is, for example, an admit discharge transfer system (hereinafter referred to as "ADT"). The ADT maintains a census of the hospital, for example, the name and status of each admitted patient. In addition to providing name and status, the ADT can also provide to the managing device 14 information such as the patient's identification number, diagnosis, allergies, emergency contact information, and proficient language.

The ADT is in communication with the managing device 14 via an industry standard translator such that updated information is available. For example, when a patient is admitted to the hospital, the ADT will communicate the newly admitted patient's information to the managing device 14. The managing device 14 can locally store the new patient's information, and present relevant portions of the information to hospital staff via an output device such as a TV, computer or LCD monitor.

It should also be appreciated that the data source is a database having staff assignment information. For example, staff assignment information includes a list of each staff member and the bed numbers for which each staff member is responsible and the communication device number associated with each staff member.

The messaging device 18 can take many different forms and be utilized in many different locations. For example, the messaging device 18 can be a pager, cell phone, intercom system display, or a display monitor. It should be appreciated that the messaging device 18 can be any device capable of receiving a text message and/or conducting two-way communication.

Figure 2:
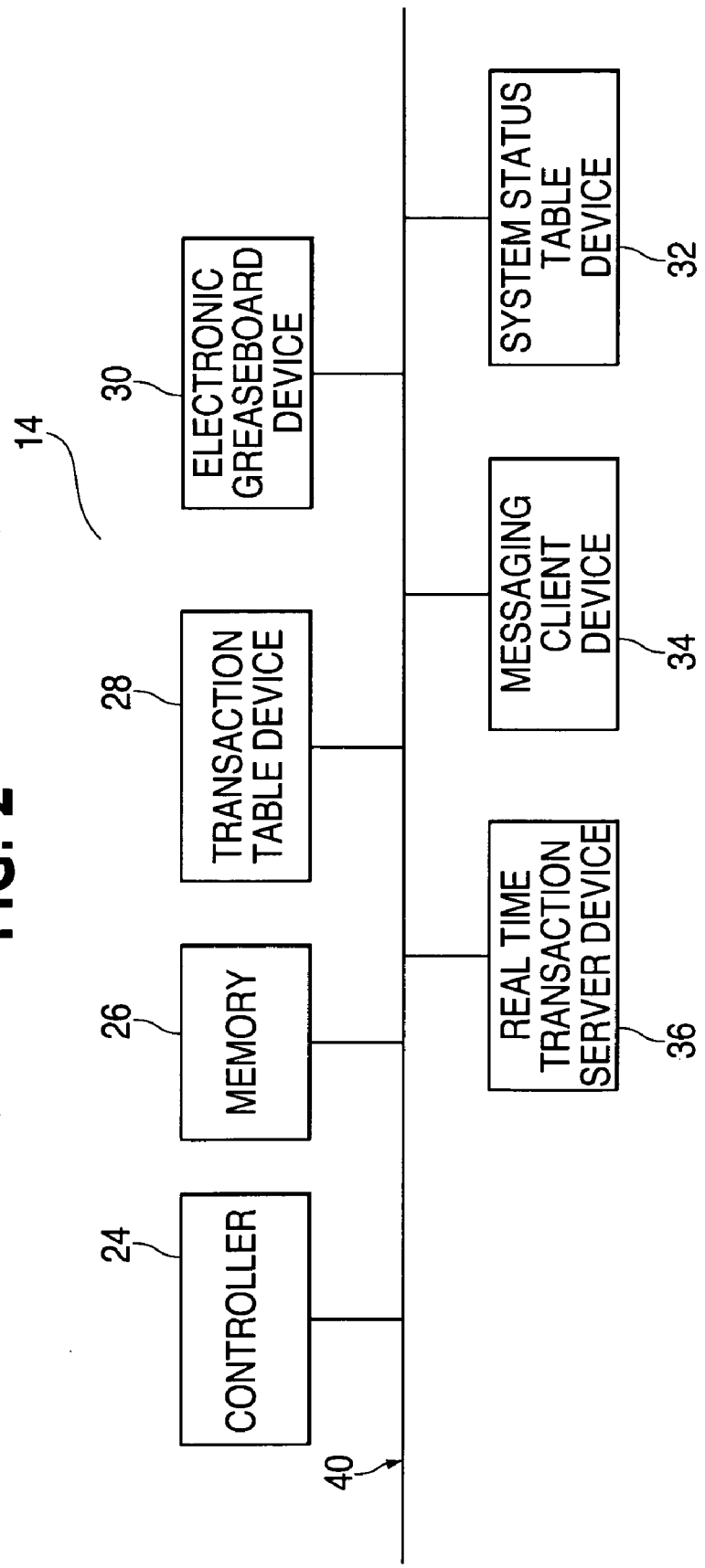
FIG. 2 is a block diagram of an apparatus capable of receiving relevant data, presenting the relevant data to users, and enabling users to construct and route an outgoing message according to the preferred embodiment of the present invention.

Referring now to FIG. 2, the managing device 14 can include, for example, a controller 24, a memory 26, a transaction table device 28, an electronic greaseboard device 30, a system status table device 32, a messaging client device 34, and a real time transaction server 36. The above mentioned components can be coupled by a control/data bus 40. Although, it should be appreciated that any other architecture, as known to those of ordinary skill in the art, may be used to couple the above mention components. It should also be appreciated that components 28-36 can take the form of software/firmware routines residing in memory 26 capable of being executed by the controller 24.

The transaction table device 28 is in constant communication with the data source 12. From the data source 12, the transaction table device 28 receives notification of individual transactions or events that are taking place throughout the hospital.

It should also be appreciated that the transaction table device 28 can received information from the electronic greaseboard device 30. For example, a staff member can manually input data into an electronic greaseboard 30. The transaction table device 28 can receive this information and update all other electronic greaseboards 30.

The electronic greaseboard device 30 maintains communication with the transaction table device 28. The electronic greaseboard device 30 presents selected portions of the data received by the transaction table device 28. In other words, the electronic grease board device 30 can be configured to present only data that corresponds with user-selected data fields. For example, the electronic greaseboard device 30 can receive data corresponding with the following fields: nurse unit, bed number, patient name, attending physician, the messaging device number associated with the attending physician, notes that are specific to the patient, currently assigned caregiver, the messaging device number associated with the currently assigned caregiver, and discharge status.

The electronic greaseboard is interactive and contains an interactive element so that users can specify the data presented and the routing destination thereof. The interactive element is capable of launching the messaging client device 34 and automatically prescribing the messaging client device 34 with specific information. For example, the user may select a particular patient name and, based on that selection, the interactive element automatically launches the messaging client device 34 pre-selected with the patient name and the routing information to the staff members responsible for the patient. The electronic greaseboard device 30 can include a plurality of monitors, each located in a position such that staff may view the monitor.

The system status table device 32 maintains communication with the transaction table device 28 and, thereby, the system status table device 32 is in sync with the transaction table device 28. The system status table device 32 maintains a compilation of all individual transactions that are received by the transaction table device 28.

In an embodiment of the present invention, the system status table device 32 categorizes the transactions received from the transaction table device 28 by assigning an information field to each transaction. For example, specific information fields can be a patient name field, a room number field, a bed number, a diagnosis field, a treating physician field, an attending staff field. Thus, upon receiving data from the transaction table device 28, the system status table device allocates the data to the corresponding information field. The system status table device 32 consists of a series of interlinked tables, where each table stores transactions of a specific information field. It should be appreciated that the transaction table device 28 is configured to receive and store information in any manner that is commonly known in the art.

From this communication with the transaction table device 28, the system status table device 32 provides an organized compilation of all transactions that have occurred in the network 10. Further, it should be appreciated that the system status table device 32 can receive information directly from the data source 12 or a device located outside of the network 10. The system status table device is also in communication with the messaging client device 34.

It should also be appreciated that the system status table can be in communication with the electronic greaseboard device 30 such that the electronic greaseboard can received an entire compilation of transactions when needed. For example, the electronic grease board device, upon initialization, can access the system status table device 32 in order to receive a snap shot of all transactions in the network. After the initial booting, the electronic greaseboard device 30 can receive updates from the transaction table device 28 without having to obtain an complete report from the system status table device 32. This also ensures that all electronic greaseboard devices 30 receive data from a common source and are thus in synch with one another.

The messaging client device 34 is a display output and a browser or resident application input. The messaging client device 34 receives information from various devices in the network 10, such as the system status table device 32 and electronic greaseboard device 30. The messaging client device 34 displays the information to an operator. Further, the messaging client device 34 enables the operator to generate a message and route the message to the messaging device 18.

For example, in operation the messaging client device 34 is capable of receiving a signal from the electronic greaseboard device 30, and based on the signal, the messaging client device 34 is capable of accessing the system status table device 32 plus pre-selecting display and routing options. The messaging client device 34 accesses the system status table device 26 to obtain all information relating to the signal. The signal can be, for example, a patient name, bed, staff member to receive the message, and device the staff member is carrying, and the messaging client device 34 obtains all information associated with those options. Also, for example, the signal can be the nursing unit in which a particular patient is located. The information provided to the messaging client device 34 thus includes a list of all beds in the nursing unit, the patient name associated with each bed, the particular staff member associated with each patient, and the routing information for messaging device 18 associated with each staff member.

The information provided to the messaging client device 34, for example, includes a list of prewritten messages relevant to that particular nursing unit, a list of all beds in the nursing unit, the patient name associated with each bed, the particular staff member associated with each patient, and the routing information for messaging device 18 associated with each staff member. The messaging client device 34 then displays all of the information obtained from the system status table device 32 to the user. The user can select among the presented information and, thereby, construct an outgoing message and assign routing information thereto.

The real time transaction server 36 receives outgoing messages from the messaging client device 34. Upon receiving the outgoing messages, the real time transaction server 36 immediately routes the outgoing messages to the messaging device 18. This provides hospital staff with immediate information such that they can quickly respond to patients.

Figure 3:
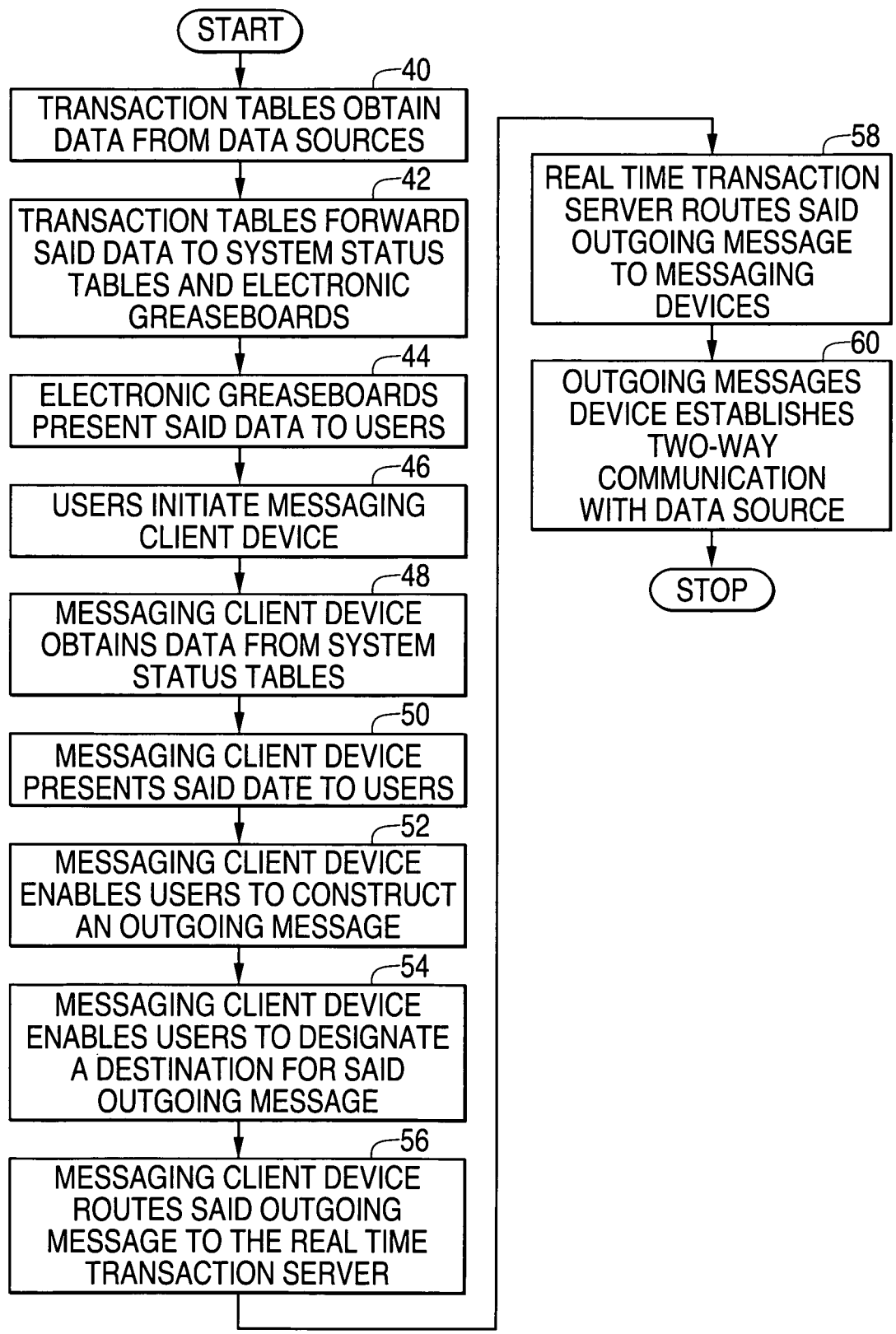
FIG. 3 is a flowchart outlining an operation for a system capable of receiving relevant data, presenting the relevant data to users, and enabling users to construct and route an outgoing message according to the preferred embodiment of the present invention.

FIG. 3 is a flowchart outlining an exemplary operation according to the present disclosure for a system capable receiving relevant data, presenting the relevant data to users, and enabling users to construct and route an outgoing message. The operation starts at step 40, where the transaction table device 28 obtains data from the data source 12. Next, in step 42, the transaction table device 28 forwards the data to the system status table device 32 and the electronic greaseboard device 30. Once the electronic greaseboard device 30 is populated, the system proceeds to step 44, where the electronic greaseboard device 30 presents the data to users.

Upon receiving the data, in step 46 an operator initiates the messaging client device 34, selecting from the electronic greaseboard device 30 the patient and/or bed, and the staff name and/or device 18 that is to receive the message. Next, in step 48, the messaging client device 34 receives the selected options, accesses the system status table device 32 where it obtains data, and in step 50 the messaging client device 34 presents the data to the operator with the options selected in the electronic greaseboard device 30 already selected in the messaging client device 34. Based on the presented data, in step 52, the operator constructs an outgoing message using the interface of the messaging client device 34. Once the message has been constructed, in step 54, the operator then selects a messaging device 18 associated with the hospital staff designated as the message recipient.

Next, in step 56, the messaging client device 34 routes the outgoing message to the real time transaction server 36. The system next performs step 58, where the real time transaction server 36 routes the outgoing message to the messaging device 18. Once the outgoing message is routed, the system proceeds to step 60 where the messaging device 18 establishes two-way communication with the data source 12.

Although the present apparatus and method is useful in hospital setting, it can also be used in other settings.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for displaying patient data and for providing messages related to patient care, comprising:
a plurality of data sources, each coupled to a network, to provide source location data and patient status data;

a managing device, coupled to the network, including:
- a transaction table device, in communication with each data source, to receive respective source location data and patient status data;
- an electronic greaseboard device, in communication with the transaction table device, to display source location data and patient status data; and
- a message generator, in communication with and initiated by the electronic greaseboard device, to generate patient care messages that include at least a patient name and message routing information; and a plurality of messaging devices, coupled to the network, to receive and display patient care messages from the message generator.

2. The system of claim 1, wherein data received by the transaction table device is at least a transaction, and the transaction table device stores a number of the transactions.

3. The system of claim 2, further comprising a system status table device in communication with the transaction table device, the electronic greaseboard device and the message generator, wherein the system status table device is configured to organize the transactions.

4. The system of claim 3, wherein the system status table device consists of a compilation of the transactions.

5. The system of claim 3, wherein the system status table device is configured to provide data to the message generator and the electronic greaseboard device.

6. The system of claim 1, wherein the message generator is configured to enable a user to manually prescribe a content and a destination for the message.

7. The system of claim 1, wherein the message generator is configured to automatically prescribe a content and a destination for the message.

8. The system of claim 1, wherein the an interactive element automatically transmits pre-selected data to the message generator.

9. The system of claim 1, wherein the message generator is configured to present data.

10. The system of claim 1, further comprising a router linked to the message generator and configured to route the message to one of the messaging devices.

11. The system of claim 1, wherein the data source is an admit discharge transfer system.

12. The system of claim 1, wherein the data source is a nurse call device.

13. The system of claim 1, wherein the data source is an automated monitoring device.

14. A method for communicating patient care messages to a caregiver, comprising:
- receiving location data and patient status data from a data source;
- storing the location data and the patient status data in a transaction table device;
- transmitting the location data and the patient status data to an electronic greaseboard device;
- displaying the location data and the patient status data to an operator;
- selecting data from the displayed data;
- generating a patient care message, based on the selected data, using a message generator, the patient care messages including at least a patient name and message routing information; and
- routing the patient care message to a messaging device for display.

15. The method of claim 14, wherein the message generator is configured to enable the operator to select among data to manually prescribe the message.

16. The method of claim 14, wherein the message generator is configured to automatically prescribe a content for the message.

17. The method of claim 14, further comprising the step of organizing data received from the transaction table device in a system status table device.

18. An apparatus for providing messages related to patient care, comprising:
- a transaction table device, coupled to a network, to receive transactions from a plurality of data sources, each transaction including source location data and patient status data;
- a system status table device, linked to the transaction table device, to organize the transactions;
- an electronic greaseboard device, linked to the transaction table device and the system status table device, to display the transactions; and
- a message generator, coupled to the network and linked to the electronic greaseboard device, to generate patient care messages for transmission over the network, the patient care messages including at least a patient name and message routing information,
- wherein, the electronic greaseboard includes an interactive element to initiate the message generator and automatically prescribe a content and a routing destination for the patient care message.

19. The apparatus of claim 18, wherein the transaction table device instantaneously provides the transactions to the electronic greaseboard device.

20. The apparatus of claim 18, wherein the system status table device is linked to the message generator and the electronic greaseboard device.

* * * * *